US012138307B2

(12) United States Patent
Baig et al.

(10) Patent No.: US 12,138,307 B2
(45) Date of Patent: Nov. 12, 2024

(54) SAPONIN EXTRACTION

(71) Applicant: GLAXOSMITHKLINE BIOLOGICALS SA, Rixensart (BE)

(72) Inventors: Ahmad Taimour Baig, Hamilton, MT (US); Juan Jose Diaz Garcia, Marietta, PA (US); Chad Austin Farrenburg, Hamilton, MT (US); Kent Raymond Myers, Hamilton, MT (US); Jeri Kay Sandvick, Hamilton, MT (US); Jeb Yeatts Vandenburg, Hamilton, MT (US)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 18/353,172

(22) Filed: Jul. 17, 2023

(65) Prior Publication Data

US 2023/0355752 A1 Nov. 9, 2023

Related U.S. Application Data

(62) Division of application No. 16/768,416, filed as application No. PCT/EP2018/083233 on Nov. 30, 2018, now Pat. No. 11,744,890.

(60) Provisional application No. 62/593,555, filed on Dec. 1, 2017.

(30) Foreign Application Priority Data

Dec. 21, 2017 (EP) .................................. 17209796

(51) Int. Cl.
*A61K 36/00* (2006.01)
*A61K 36/185* (2006.01)
*A61K 39/39* (2006.01)
*A61K 39/00* (2006.01)

(52) U.S. Cl.
CPC ............ *A61K 39/39* (2013.01); *A61K 36/185* (2013.01); *A61K 2039/55577* (2013.01); *A61K 2236/331* (2013.01)

(58) Field of Classification Search
CPC .......................................... A61K 2039/55577
See application file for complete search history.

(56) References Cited

U.S. PATENT DOCUMENTS

| 5,057,540 A | 10/1991 | Kensil et al. |
| 6,231,859 B1 | 5/2001 | Kensil |
| 6,916,476 B1 | 7/2005 | Livingston |
| 11,591,364 B2 | 2/2023 | Baig et al. |

FOREIGN PATENT DOCUMENTS

| CL | 2011003113 A1 | 8/2012 |
| CL | 2020001439 A1 | 2/2021 |
| CL | 2020001440 A1 | 2/2021 |
| JP | 2001505573 A | 4/2001 |
| JP | 2015522643 A | 8/2015 |
| JP | 2020529565 A | 10/2020 |
| JP | 2020529601 A | 10/2020 |
| WO | 8809336 A1 | 12/1988 |
| WO | 9632401 A1 | 10/1996 |
| WO | 1998024319 A1 | 6/1998 |
| WO | 1999053933 A1 | 10/1999 |
| WO | 2007068907 A2 | 6/2007 |
| WO | 2010142685 A1 | 12/2010 |
| WO | 2014016374 A1 | 1/2014 |
| WO | 2019025520 A1 | 2/2019 |
| WO | 2019047150 A1 | 3/2019 |
| WO | 2019106191 A1 | 6/2019 |
| WO | 2019106192 A1 | 6/2019 |

OTHER PUBLICATIONS

International Search Report and Written Opinion in corresponding International Application No. PCT/EP2018/083234 mailed Feb. 14, 2019 (11 pages).
Chaicharoewnpong and Petsom, Phytochemical Analysis, Mar. 2009, 20:253-255.
Higuchi et al., "An acylated triterpenold saponin from Quillaja saponaria", Phytochemistry, 27: 1165-1168 (1988).
Ragupathi et al., "Natural and synthetic saponin adjuvant QS-21 for vaccines against cancer", Expert Review of Vaccines, 10:463-470 (2011).
Thalhamer et al., "Characterization of quillaja bark extracts and evaluation of their purity using liquid chromatography-high resolution mass spectrometry", Phytochemistry Letters, 8: 97-100 (2014).
Sen et al., (1998), "Effect of Quillaja saponaria saponins and Yucca schidigera plant extract on growth of *Escherichia coli*", Letters in Applied Microbiology, 27(1), pp. 35-38.
Chipley, J. R. (2005), "Sodium benzoate and benzoic acid", Antimicrobials in Food, A.L. Branen, J.N. Sofos, and P.M. Davidson (Eds.) pp. 11-48. Taylor Francis Group.
International Search Report and Written Opinion in corresponding International Application No. PCT/EP2018/083233 mailed Mar. 8, 2019 (9 pages).
Gilabert-Oriol et al., "Electrophoretic mobility as a tool to separate immune adjuvant saponins from Quillaja saponaria Molina", International Journal of Pharmaceutics, 487: 39-48 (2015).
Tippel et al., "Composition of Quillaja saponin extract affects lipid oxidation in oil-in-water emulsions", Food Chemistry, 221: 386-394 (2017).
Marty-Roix et al., "Identification of QS-21 as an Inflammasome-activating molecular component of saponin adjuvants", Journal of Biological Chemistry, 291: 1123-1136 (2016).
Brunner et al., "QS-21 adjuvant: laboratory scale purification method and formulation into liposomes", Methods in Molecular Biology, 1494: 73-86 (2016).

(Continued)

*Primary Examiner* — Qiuwen Mi

(57) ABSTRACT

Crude aqueous extracts of *Quillaja saponaria* Molina containing at least the QS-21 main peak and 2018 component, wherein the ratio of 2018 component/QS-21 main peak is ≤0.075, as measured by UV absorbance at 214 nm, methods for obtaining such extracts and related aspects.

42 Claims, 6 Drawing Sheets

(56) References Cited

OTHER PUBLICATIONS

Sewliker et al., "Antimicrobial Effects of Quillaja saponaria Extract against *Escherichia coli* O157:H7 and the Emerging Non-O157 Shiga Toxin-Producing *E. coli*," Journal of Food Science, vol. 92, No. 5, (2017), pp. 1171-1177.

Geoffrey C. Kite, et al. "Metabolomic analysis of saponins in crude extracts of Quillaja saponaria by liquid chromatography/mass spectrometry for product authentication," Rapid Comunications in Mass Spectrometry, 2004, vol. 18, pp. 2859-2870.

Shengjun Guo et al., "Triterpenoid Saponins from Quillaja saponaria," Phytochemistry, 1998, vol. 48, No. 2, pp. 175-180.

Lars Nord et al., "Separation and Structural Analysis of Saponins in a Bark Extract from Quillaja saponaria Molina," Carbohydrate Research, 1999, vol. 321, Issues 1-2, pp. 70-81.

Lars Nord et al., "Novel Acetylated Triterpenoid Saponins in a Chromatographic Fraction from Quillaja saponaria Molina," Carbohydrate Research, (2000), vol. 329, Issue 4, pp. 817-829.

Johan Bankefors et al., "Structural Classification of Acyl-Substituted Quillaja saponins by Electrospray Ionisation Ion Trap Multiple-Stage Mass Spectrometry in Combination with Multivariate Analysis," Rapid Commun. Mass Spectrom., (2008), vol. 22, pp. 3851-3860.

U.S. Appl. No. 18/098,949, filed Jan. 19, 2023.

FIG. 4

| Experiment | Temperature (°C) | pH | Sodium benzoate (g/L) | Δ(2018/QS-21) ratio after 3h |
|---|---|---|---|---|
| 8 | 40 | 3.8 | 0 | (-0.0009) |
| 16 | 60 | 3.8 | 0 | 0.0044 |
| 12 | 86 | 3.8 | 0 | 0.0495 |
| 14 | 40 | 4.5 | 0 | 0.0010 |
| 3 | 60 | 4.5 | 0 | 0.0012 |
| 18 | 86 | 4.5 | 0 | 0.0238 |
| 5 | 40 | 5.2 | 0 | 0.0004 |
| 10 | 60 | 5.2 | 0 | 0.0020 |
| 1 | 86 | 5.2 | 0 | 0.0131 |
| 4 | 40 | 3.8 | 1 | (-0.0003) |
| 6 | 60 | 3.8 | 1 | 0.0050 |
| 2 | 86 | 3.8 | 1 | 0.0389 |
| 7 | 40 | 4.5 | 1 | (-0.0005) |
| 13 | 60 | 4.5 | 1 | (-0.0007) |
| 9 | 86 | 4.5 | 1 | 0.0188 |
| 17 | 40 | 5.2 | 1 | 0.0002 |
| 15 | 60 | 5.2 | 1 | 0.0009 |
| 11 | 86 | 5.2 | 1 | 0.0116 |

SAPONIN EXTRACTION

CROSS-REFERENCE TO RELATED APPLICATIONS

This application is a Division of U.S. application Ser. No. 16/768,416, filed May 29, 2020, which is a National Stage Application under 35 U.S.C. § 371 of International Application No. PCT/EP2018/083233, filed Nov. 30, 2018, which: 1) claims the benefit under 35 U.S.C. § 119 (e) of U.S. Provisional Application No. 62/593,555, filed Dec. 1, 2017 and 2) claims priority under 35 U.S.C. § 119 (b) to EP application Ser. No. 17/209,796.6, filed Dec. 21, 2017. All of the above-listed applications are hereby incorporated by reference in their entireties.

TECHNICAL FIELD

The present application generally relates to saponin extracts, in particular crude aqueous extracts of *Quillaja saponaria* Molina, methods for their manufacture and to associated aspects.

BACKGROUND OF THE INVENTION

Adjuvants are included in vaccines to improve humoral and cellular immune responses, particularly in the case of poorly immunogenic subunit vaccines. Similar to natural infections by pathogens, adjuvants rely on the activation of the innate immune system to promote long-lasting adaptive immunity.

The Adjuvant System 01 (AS01) is a liposome-based adjuvant which contains two immunostimulants, 3-O-desacyl-4'-monophosphoryl lipid A (3D-MPL) and QS-21 (Garcon and Van Mechelen, 2011; Didierlaurent et al., 2017). 3D-MPL is a non-toxic derivative of the lipopolysaccharide from *Salmonella minnesota* which is a TLR4 agonist) and QS-21 is a natural saponin extract from the bark of the South American tree *Quillaja saponaria* Molina (Kensil et al., 1991; Ragupathi et al., 2011). AS01 is included in the recently developed vaccines for malaria (RTS,S—Mosquirix®) and Herpes zoster (HZ/su—Shingrix®), and in multiple candidate vaccines in development against pathogens such as human immunodeficiency virus and *Mycobacterium tuberculosis*.

AS01 injection results in rapid and transient activation of innate immunity in animal models. Neutrophils and monocytes are rapidly recruited to the draining lymph node (dLN) upon immunization. Moreover, AS01 induces recruitment and activation of MHCII$^{high}$ dendritic cells (DC), which are necessary for T cell activation (Didierlaurent A. M. et al., 2014). Some data are also available on the mechanism of action of the components of AS01. 3D-MPL signals via TLR4, stimulating NF-κB transcriptional activity and cytokine production and directly activates antigen-presenting cells (APCs) both in humans and in mice (De Becker et al., 2000; Ismaili et al., 2002; Martin et al., 2003; Mata-Haro et al., 2007). QS-21 promotes high antigen-specific antibody responses and CD8$^+$ T-cell responses in mice (Kensil and Kammer, 1998; Newman et al., 1992; Soltysik et al., 1995) and antigen-specific antibody responses in humans (Livingston et al., 1994). Because of its physical properties, it is thought that QS-21 might act as a danger signal in vivo (Lambrecht et al., 2009; Li et al., 2008). Although QS-21 has been shown to activate ASC-NLRP3 inflammasome and subsequent IL-1β/L-18 release (Marty-Roix, R. et al., 2016), the exact molecular pathways involved in the adjuvant effect of saponins have yet to be clearly defined.

As with any component of a product which is approved as a human medicament, production of QS-21 requires the use of approved manufacturing processes and careful control of final composition to ensure that it meets the required specification. Modification of existing processes requires costly and time consuming re-validation, yet deviations from specification also result in waste. There is a continuing need for robust methods for the manufacture of QS-21 and for QS-21 material of defined composition.

SUMMARY OF THE INVENTION

In a first aspect, the present invention provides a crude aqueous extract of *Quillaja saponaria* Molina containing at least the QS-21 main peak and 2018 component, wherein the ratio of 2018 component/QS-21 main peak is ≤0.075, as measured by UV absorbance at 214 nm.

In a second aspect, the present invention provides a crude aqueous extract of *Quillaja saponaria* Molina containing

QS-21AV2

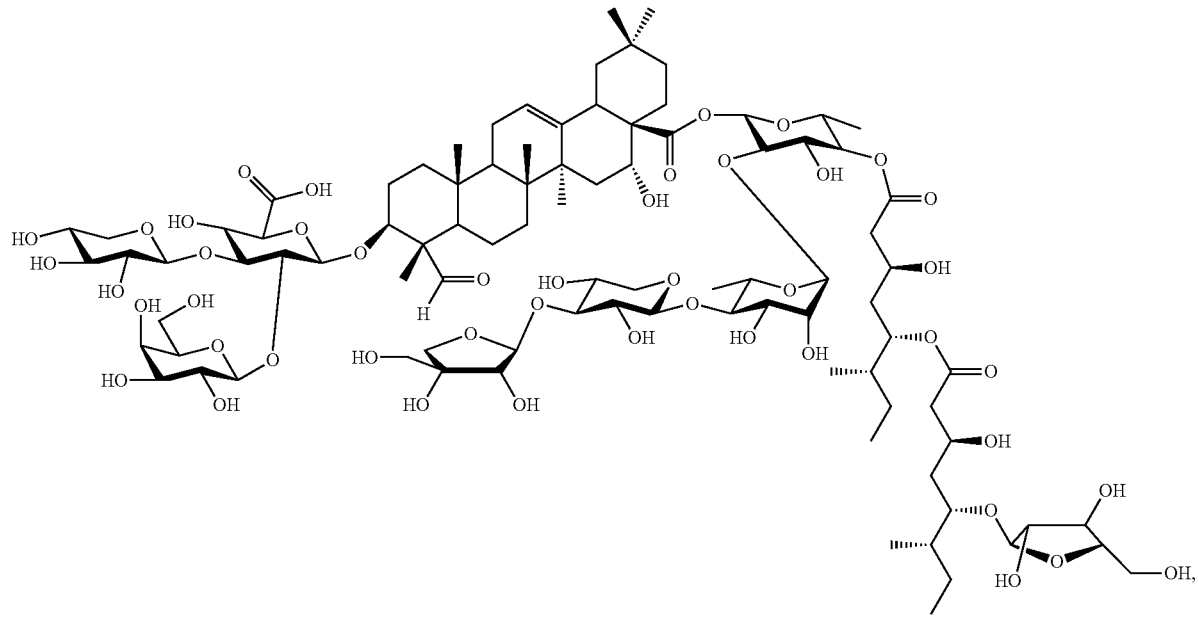

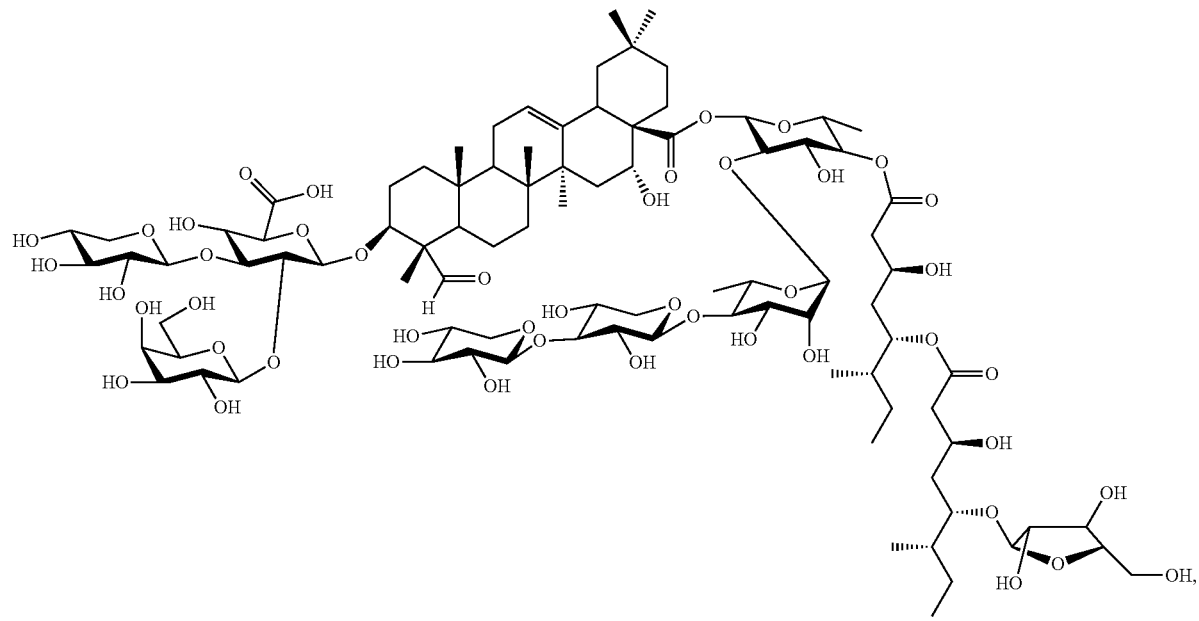
QS-21AV2
1856 component:
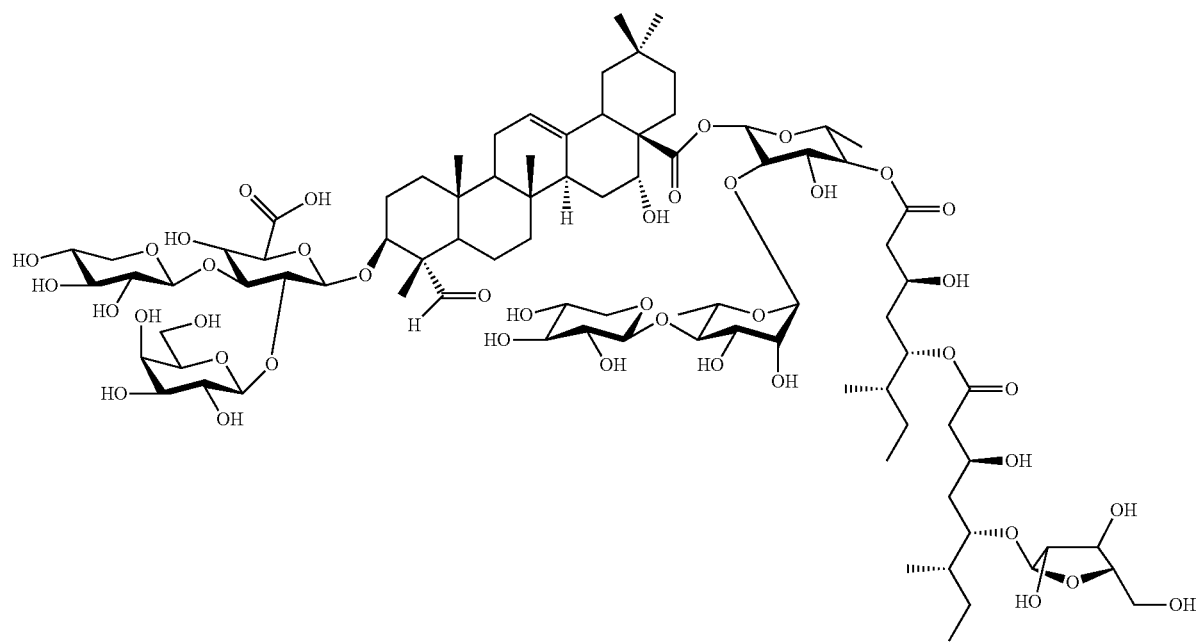

and
2002 component:
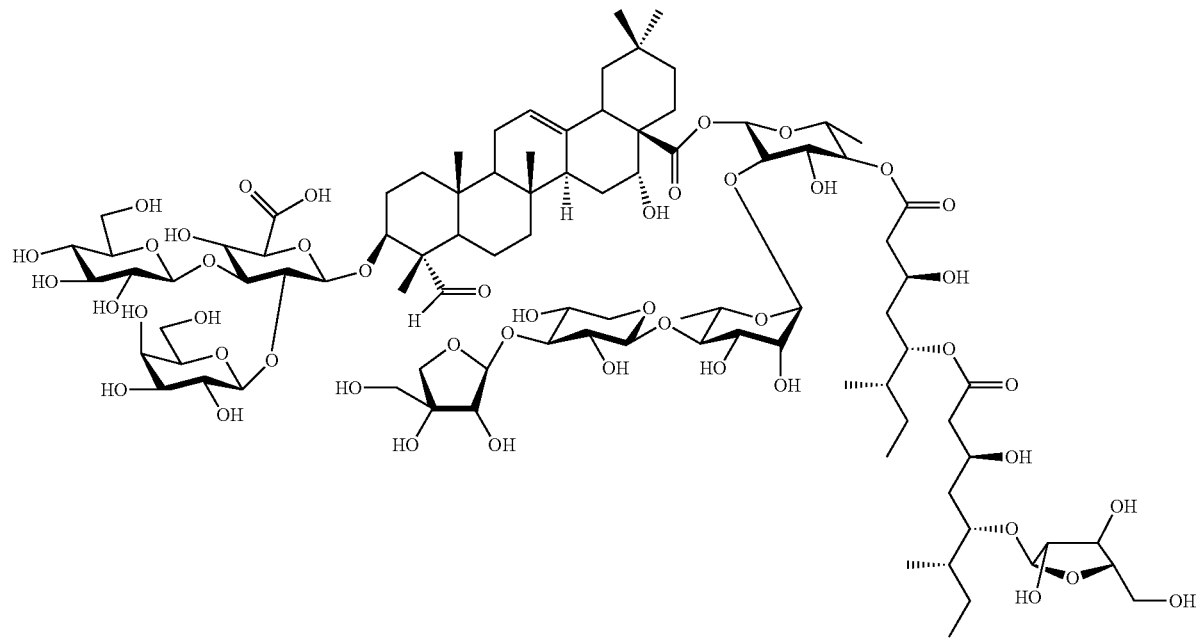
(collectively referred to as QS-21 main peak components), and 2018 component:
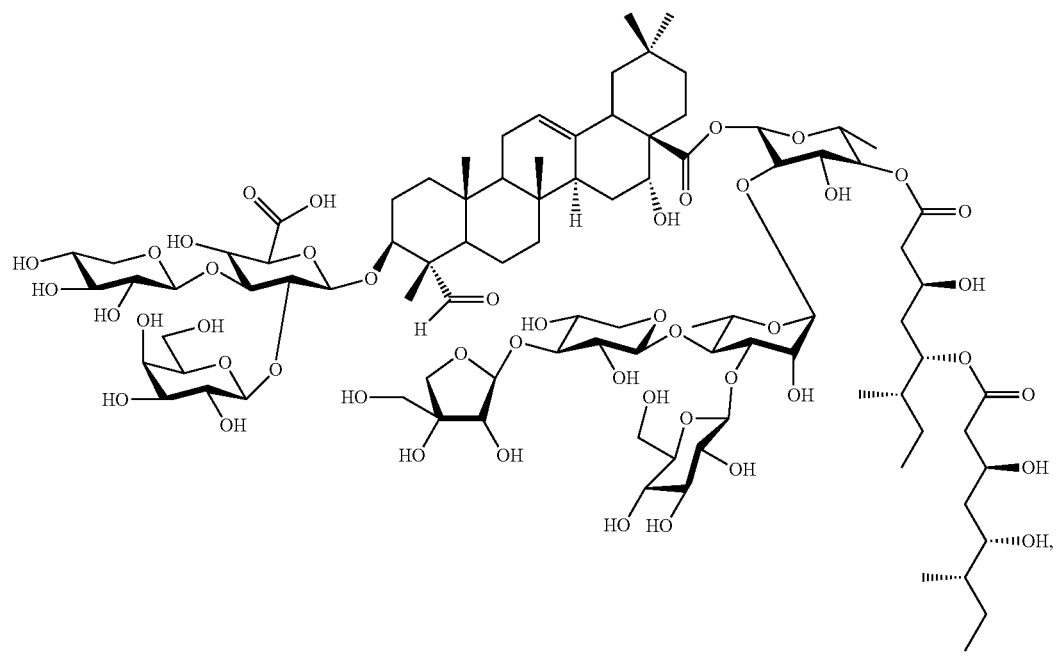

wherein the ratio 2018 component/QS-21 main peak components is ≤0.075, as measured by UV absorbance at 214 nm.

In a third aspect, the present invention provides a method for preparing a crude aqueous extract of *Quillaja saponaria* Molina comprising the following steps:
 a) selecting *Quillaja saponaria* Molina material having an appropriate 2018 component content,
 b) preparing an aqueous extract from the material under conditions wherein 2018 component generation is controlled.

DETAILED DESCRIPTION

As mentioned previously, any component of a product which is authorised as a human medicament requires the use of approved manufacturing processes and careful control of final composition to ensure that it meets the required specification. Deviations from specification result in waste. However, safety and efficacy investigation relies upon the testing of defined compositions, therefore adaptation of component specifications introduces risk. Modification of existing processes requires costly and time consuming re-validation.

The present inventors have found that crude aqueous extracts of *Quillaja saponaria* Molina vary in composition, in particular with respect to a component referred to herein as the 2018 component, and that it is difficult to separate excess 2018 component by applying existing approved manufacturing processes. Consequently, the present invention provides methods for achieving a crude aqueous extract of *Quillaja saponaria* Molina of a defined composition, suitable for the preparation of consistent purified extracts following further processing.

Variation in composition may be due to natural deviations in the source material and/or due to conditions applied when extracting the saponins to obtain the crude aqueous extract. The inventors developed a crude aqueous extract of *Quillaja saponaria* Molina of defined composition, in particular in terms of the 2018 component content as compared to the content of components of principal interest. Said crude aqueous extract advantageously provides a suitable starting material with which to obtain a purified saponin extract which is particularly suitable for use as an immunostimulant providing an efficient immune response and an acceptable level of reactogenicity when formulated with an antigen and administered to a subject.

Quil A is a saponin preparation isolated from the South American tree *Quillaja saponaria* Molina and was first described as having adjuvant activity by Dalsgaard et al. in 1974 ("Saponin adjuvants", Archiv. für die gesamte Virusforschung, Vol. 44, Springer Verlag, Berlin, p 243-254). Purified fractions of Quil A have been isolated by HPLC which retain adjuvant activity without the toxicity associated with Quil A (see, for example, EP0362279). Various fractions have been found to have adjuvant activity, such as QS-7, QS-17, QS-18 and QS-21, although their toxicity varies considerably.

By the term 'saponin extract' as used herein is meant an extract of *Quillaja saponaria* Molina.

By the term 'triterpenoid glycosides' as used herein is meant an entity or entities having a triterpenoid core derivatised by sugars which are attached via glycosidic bonds.

Figure 3:
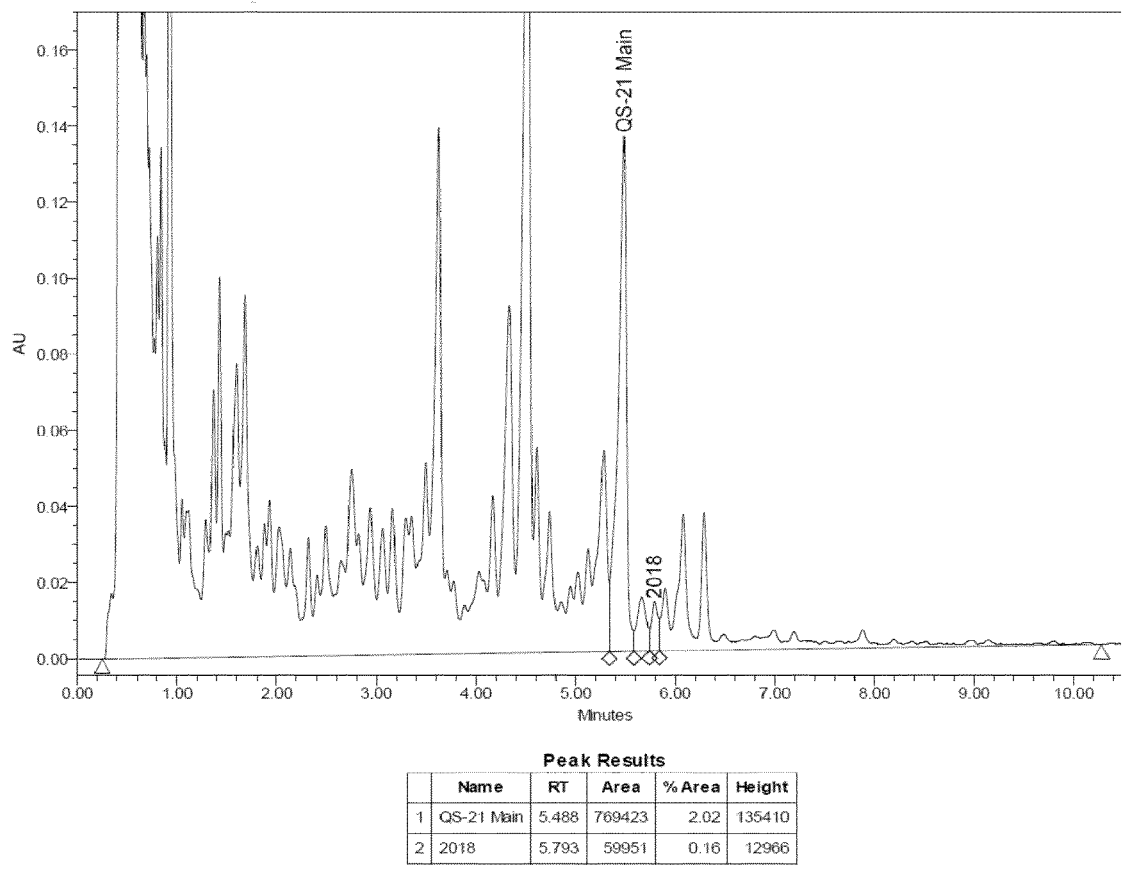
FIG. 3: UPLC-UV chromatogram of a crude aqueous *Quillaja saponaria* Molina bark extract FIG. 4 Tabulation of experimental conditions and observed impact on 2018 component/QS-21 main peak ratio FIG. 5 Surface plot of observed impact on 2018 component/QS-21 main peak ratio arising from pH and temperature conditions FIG. 6 Impact of temperature on 2018 component to QS-21 main peak ratio over time at pH 3.8

By the term '2018 component' is meant the triterpenoid glycosides identified as '2018' in FIG. 3. Suitably the 2018 component in the UPLC-UV methods described herein may be identified with a retention time of approximately 5.8 min, and the primary component of the peak having a monoisotopic molecular weight of 2017.9. The primary 2018 component has been identified as having the putative structure

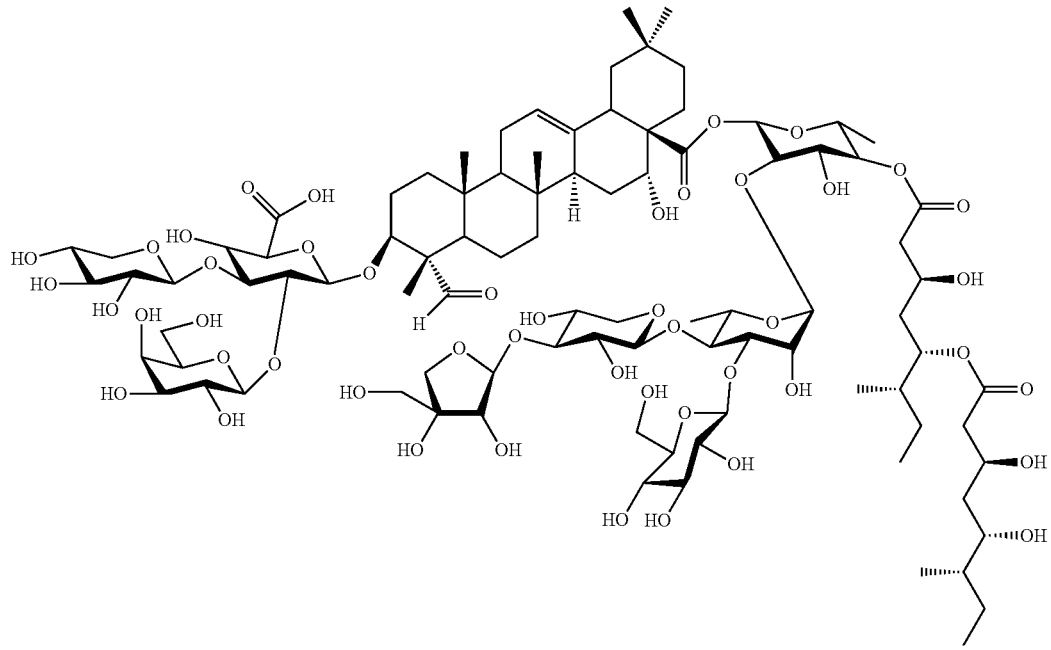

by MS/MS.

By the term '1988 component' is meant the triterpenoid glycosides identified as part of the QS-21 main peak in FIG. 3 and having a monoisotopic molecular weight of 1987.9. The 1988 component may consist of
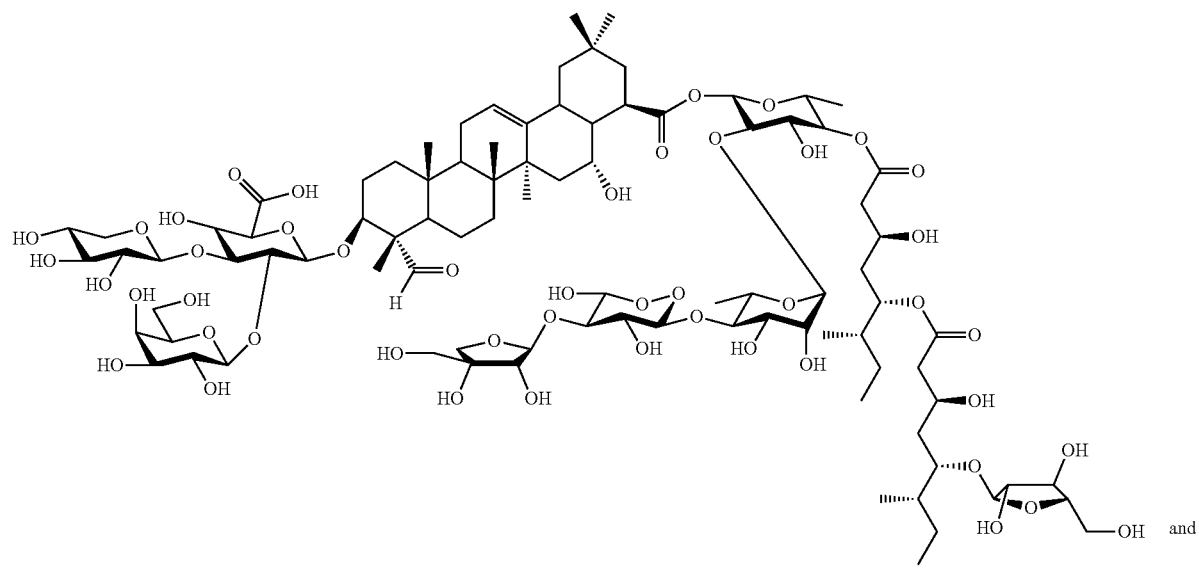
QS-21A V1
and
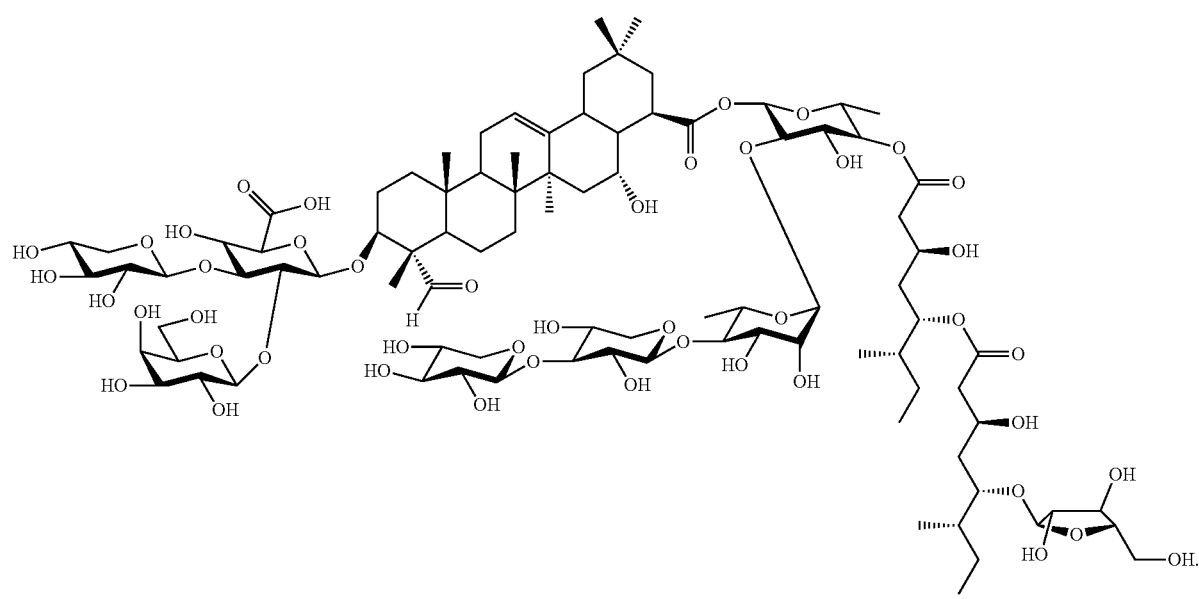
QS-21A V2

By the term '1856 component' is meant the triterpenoid glycosides identified as part of the QS-21 main peak in FIG. 3 and having a monoisotopic molecular weight of 1855.9. The 1856 component may consist of:

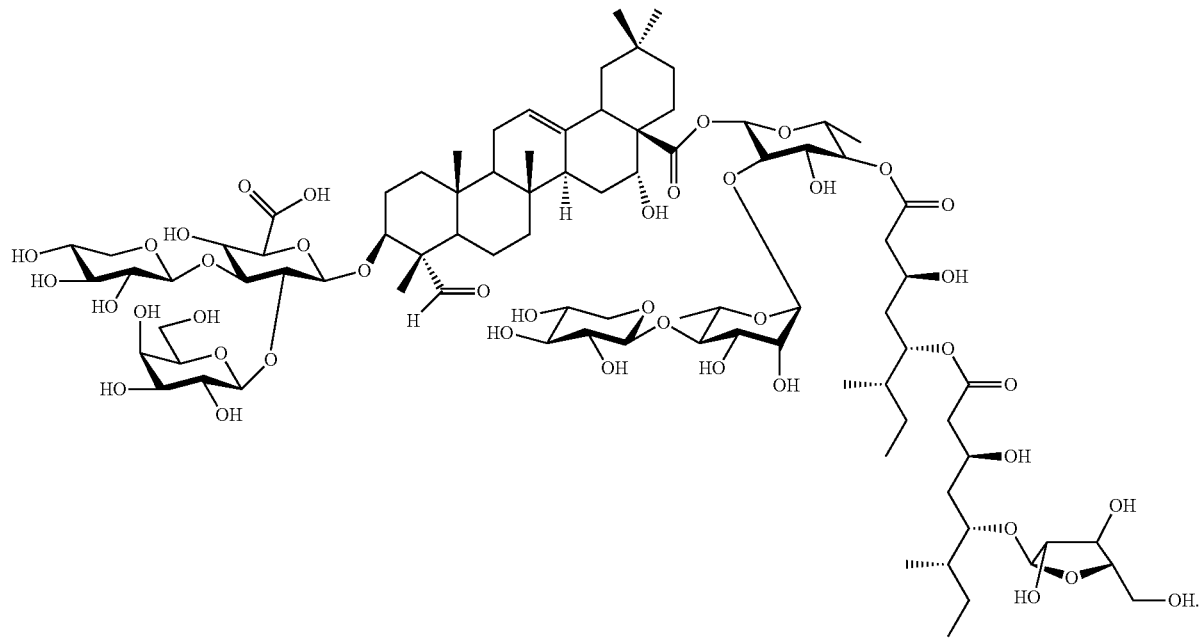

By the term '2002 component' is meant the triterpenoid glycosides identified as part of the QS-21 main peak in FIG. 3 and having a monoisotopic molecular weight of 2001.9. The 2002 component has been identified as having the putative structure:

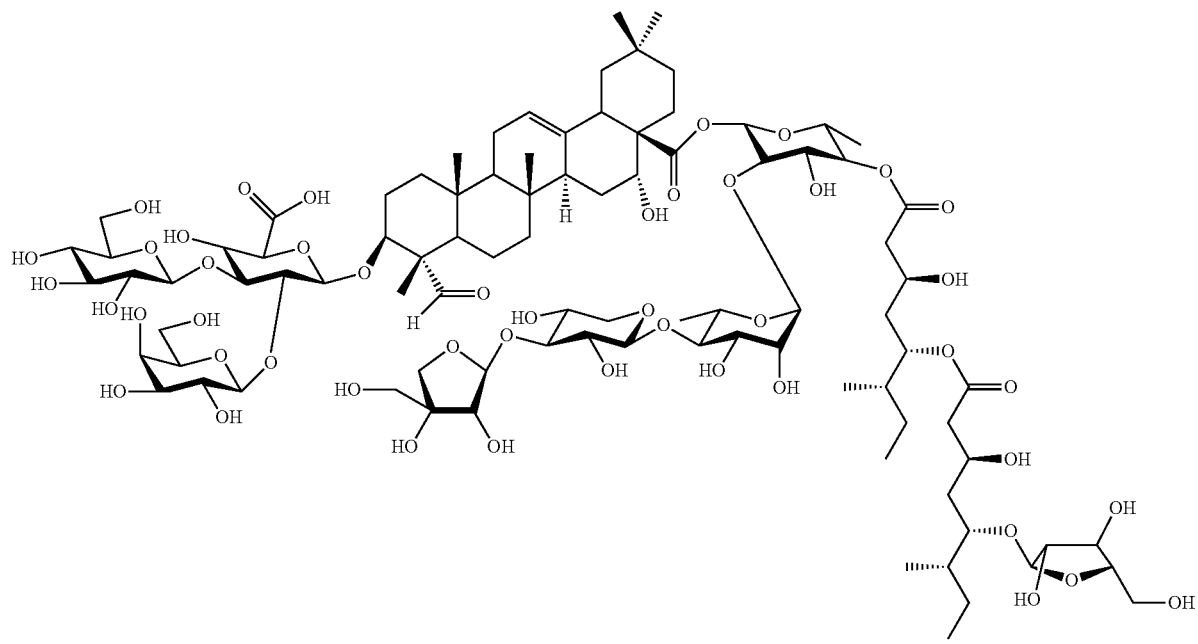

by MS/MS.

Limitations of the MS/MS technique in differentiating certain branching, stereochemistry and isomeric sugar species (e.g. apiose and xylose) means that some structures are putative and based on an assumed conserved core. Putative structures should therefore be taken to mean the actual structure of the entity which has otherwise been identified, in the event the putative structure is incorrect.

Monoisotopic molecular weights are determined by negative ion electrospray mass spectrometry.

Figure 2:
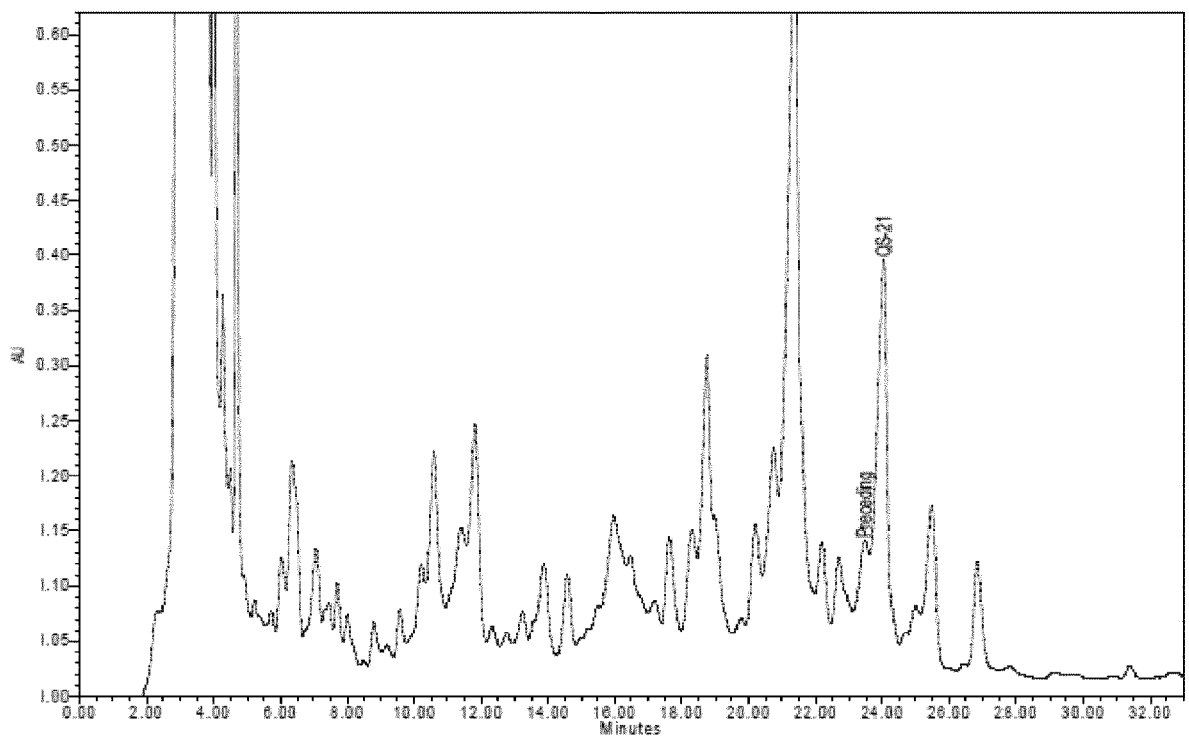
FIG. 2: HPLC-UV chromatogram of a crude aqueous *Quillaja saponaria* Molina bark extract

By the term 'QS-21 main peak' is meant the triterpenoid glycosides identified as 'QS-21' and 'QS-21 Main' in FIG. 2 or FIG. 3 respectively. Suitably QS-21 has the principal molecular weight components of 1855.9, 1987.9 and 2001.9 m/z. The QS-21 main peak may consist primarily of

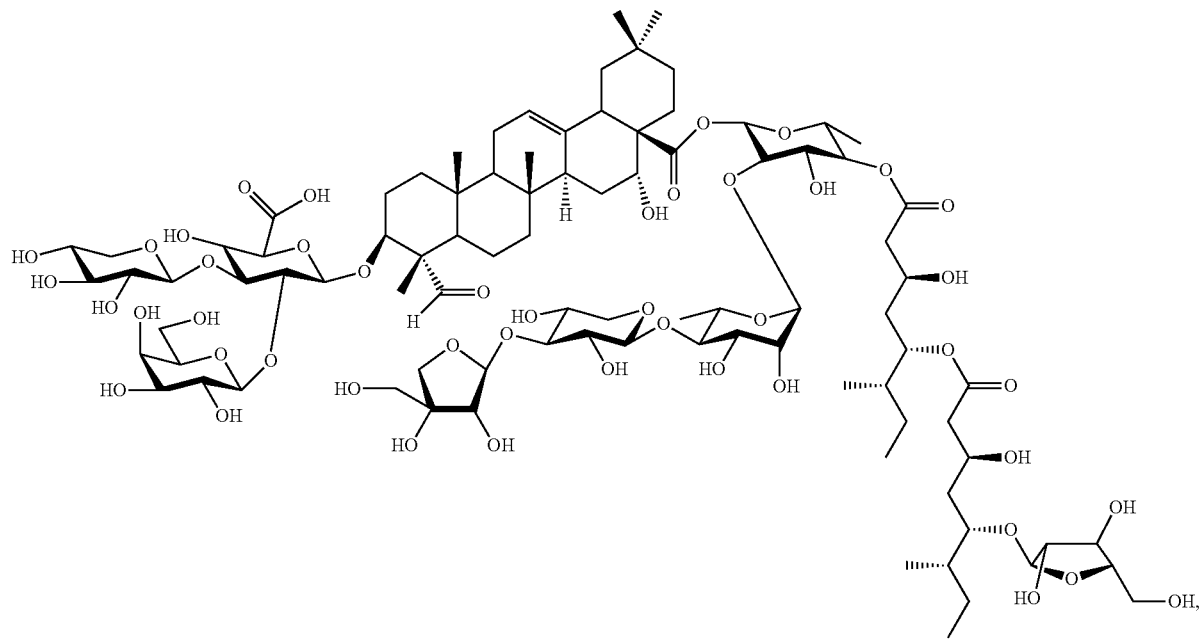

QS-21A V1

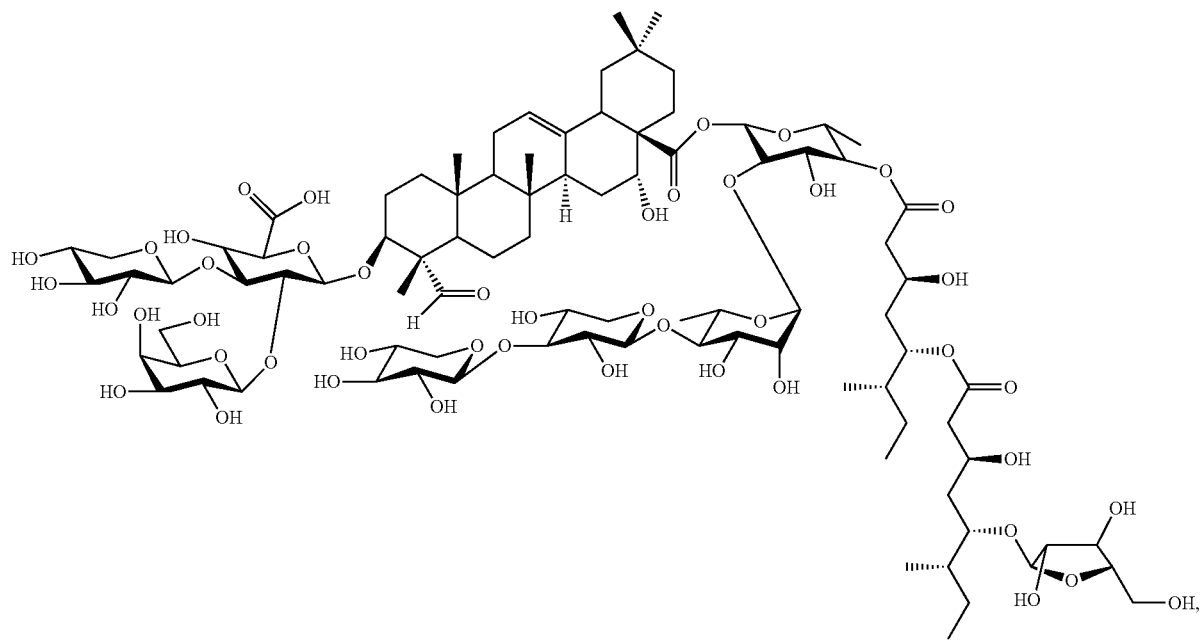

QS-21A V2

1856 component:

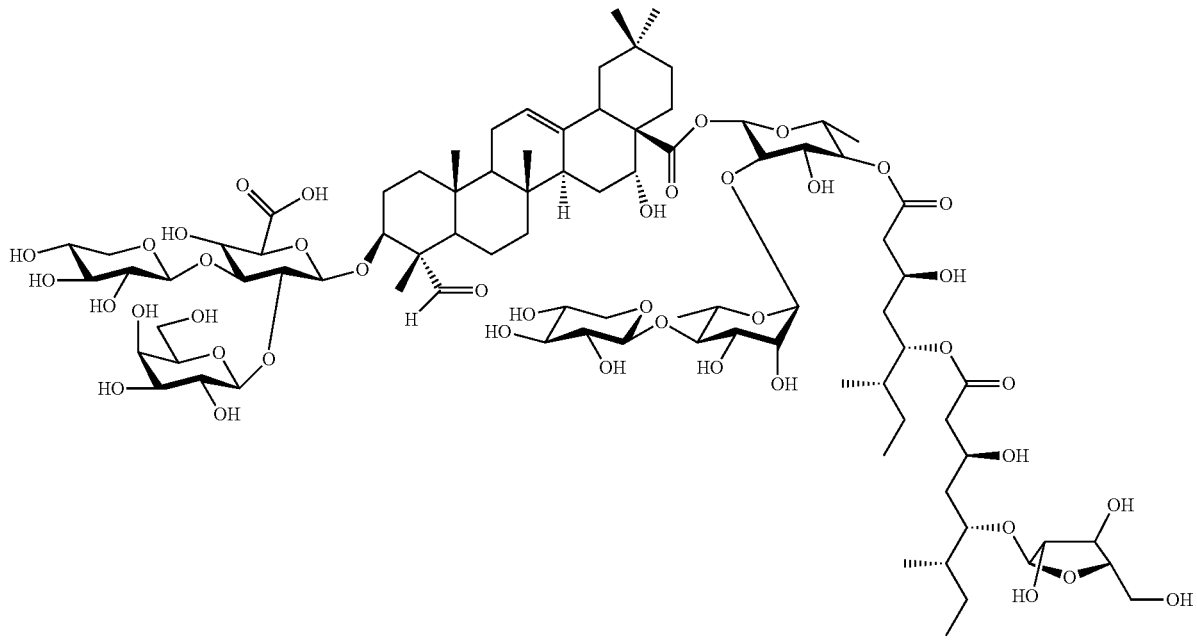

and
2002 component:

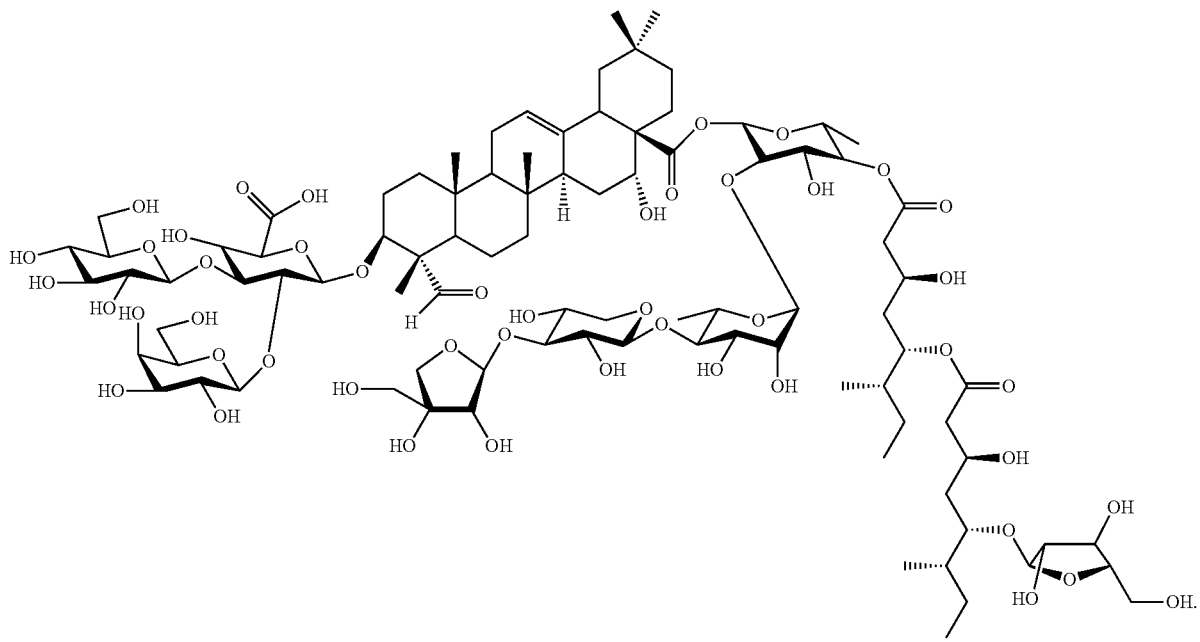

By the term 'Preceding peak' is meant the peak immediately preceding the QS-21 main peak in the HPLC-UV methods described herein (see FIG. 2).

By the term 'dried' is meant that substantially all solvent has been removed. A dried extract will typically contain less than 5% solvent w/w (such as less than 5% water w/w). Suitably the dried extract will contain 100 ppm or less acetonitrile (w/w).

The crude aqueous extract of *Quillaja saponaria* Molina is obtained by aqueous extraction (but need not be in aqueous form, e.g. it may subsequently have been dried, subjected to solvent exchange or reconstituted into a different solvent).

In a first aspect, the present invention provides a crude aqueous extract of *Quillaja saponaria* Molina containing at least the QS-21 main peak and 2018 component, wherein the ratio of 2018 component/QS-21 main peak is ≤0.075, as measured by UV absorbance at 214 nm. Suitably the ratio of 2018 component/QS-21 main peak is ≤0.064, as measured by UV absorbance at 214 nm. Desirably the ratio of 2018 component/QS-21 main peak is at least 0.005, such as at least 0.01 as measured by UV absorbance at 214 nm.

Suitably the Preceding peak to QS-21 main peak ratio is 0.45 or lower, in particular 0.4 or lower (as determined by HPLC-UV absorbance at 214 nm). The Preceding peak to QS-21 main peak ratio may be 0.05 or higher, in particular 0.1 or higher (as determined by HPLC-UV absorbance at 214 nm).

Typically the crude extract is a bark extract of *Quillaja saponaria* Molina. Accordingly, suitably the crude extract is obtained from *Quillaja saponaria* Molina bark.

Suitably the QS-21 main peak content in an aqueous solution of crude aqueous extract of *Quillaja saponaria* Molina is at least 1 g/L, such as at least 2 g/L, especially at least 2.5 g/L and in particular at least 2.8 g/L (e.g. as determined by UV absorbance relative to a control sample of known concentration).

In a second aspect, the present invention provides a crude aqueous extract of *Quillaja saponaria* Molina containing:

QS-21A V1

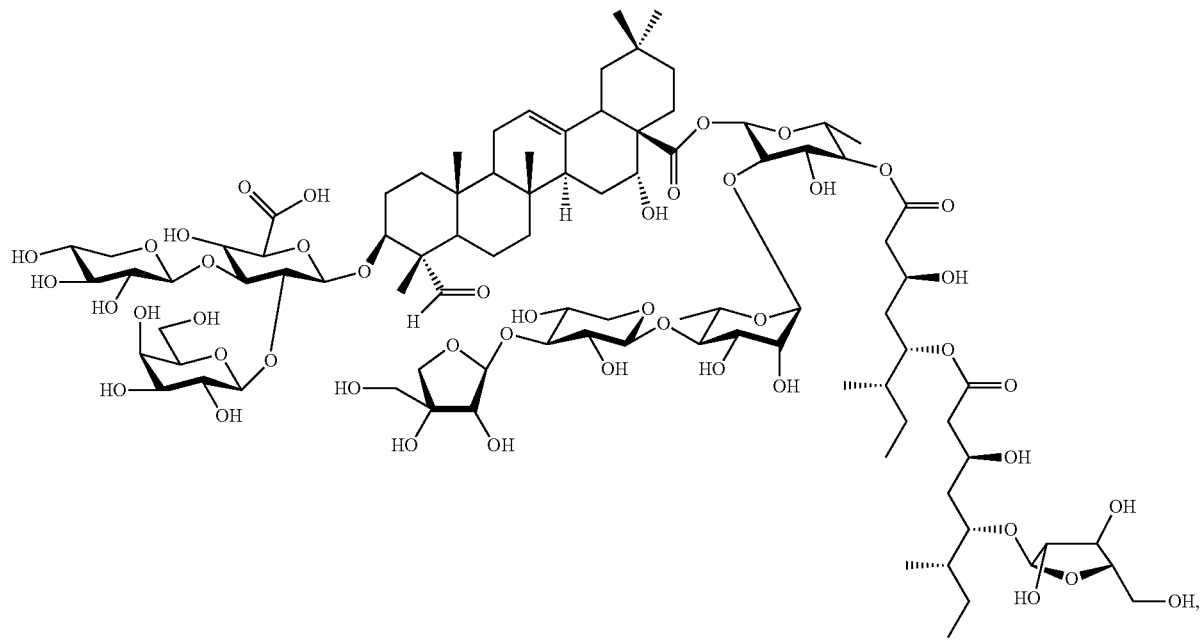

QS-21A V2

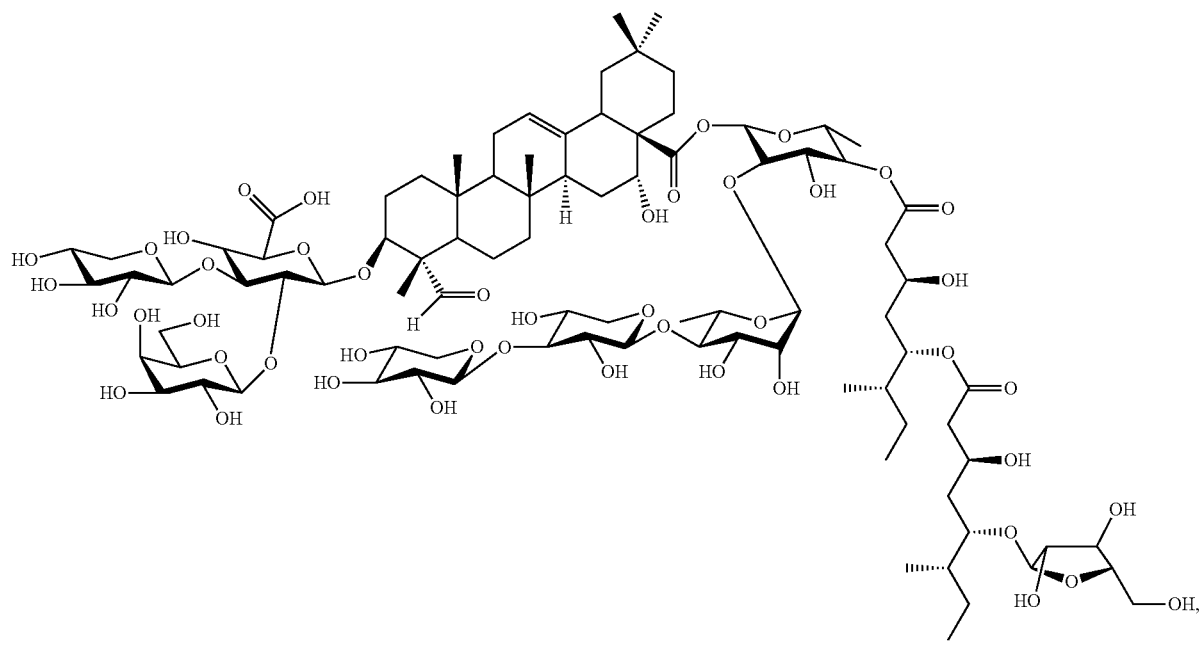

1856 component:
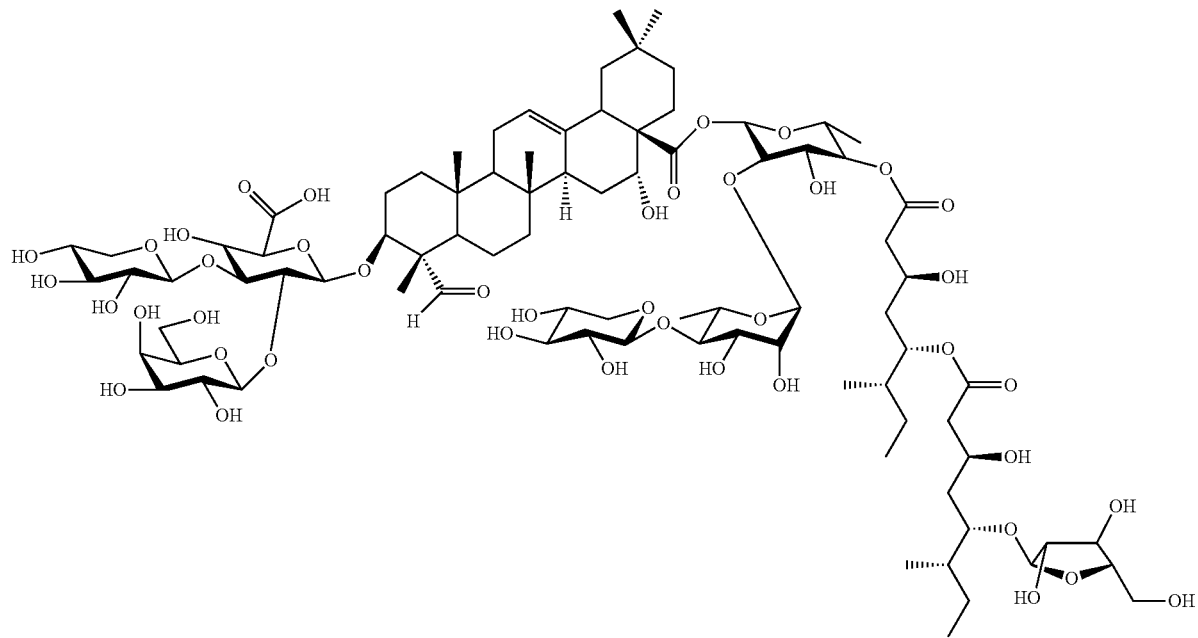
and
2002 component:
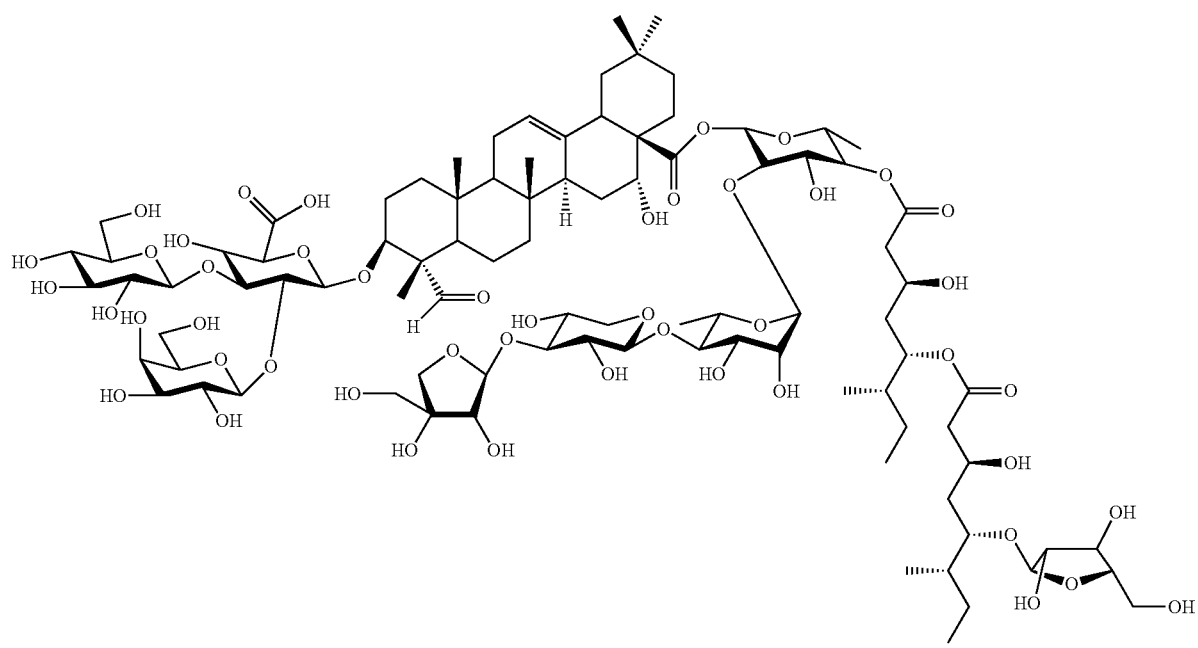

(collectively referred to as QS-21 main peak components), and 2018 component:

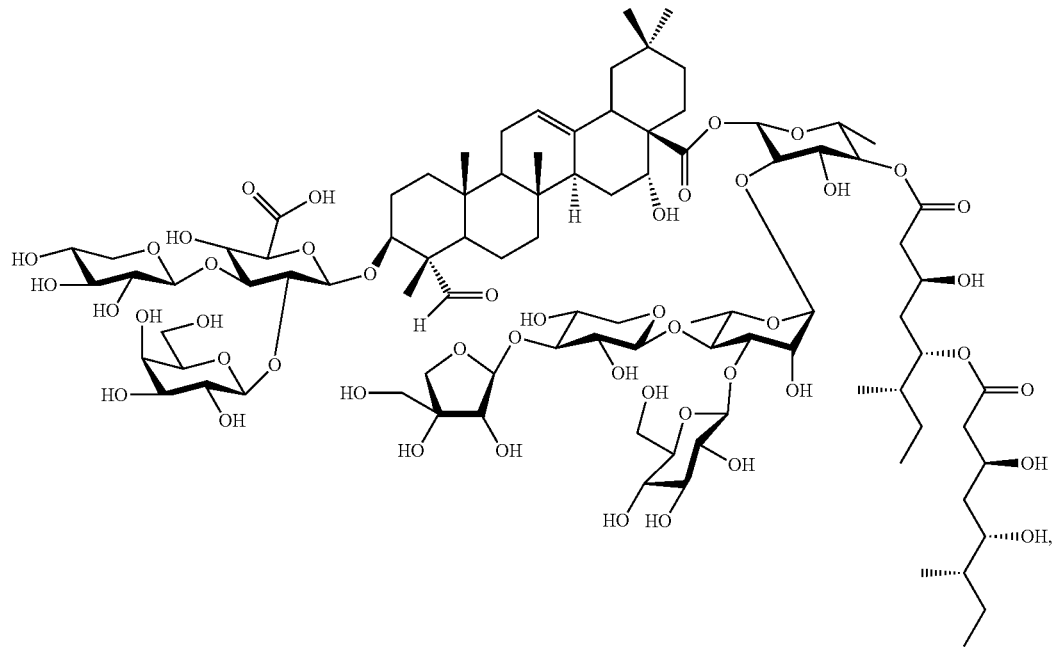

wherein the ratio of 2018 component/QS-21 main peak components is ≤0.075, as measured by UV absorbance at 214 nm.

Suitably the ratio 2018 component/QS-21 main peak components is ≤0.064, as measured by UV absorbance at 214 nm. Desirably the ratio of 2018 component/QS-21 main peak components is at least 0.005, such as at least 0.01 as measured by UV absorbance at 214 nm.

Suitably the Preceding peak to QS-21 main peak ratio is 0.45 or lower, in particular 0.4 or lower (as determined by HPLC-UV absorbance at 214 nm). The Preceding peak to QS-21 main peak ratio may be 0.05 or higher, in particular 0.1 or higher (as determined by HPLC-UV absorbance at 214 nm).

Typically the crude extract is a bark extract of *Quillaja saponaria* Molina. Accordingly, suitably the crude aqueous extract of the invention is obtained from *Quillaja saponaria* Molina bark.

Suitably the QS-21 main peak content in an aqueous solution of crude aqueous extract of *Quillaja saponaria* Molina is at least 1 g/L, such as at least 2 g/L, especially at least 2.5 g/L and in particular at least 2.8 g/L (e.g. as determined by UV absorbance relative to a control sample of known concentration).

Saponin Extraction

In a third aspect, there is provided a method for preparing a crude aqueous extract of *Quillaja saponaria* Molina comprising the following steps:
  a) selecting *Quillaja saponaria* Molina material having an appropriate 2018 component content,
  b) preparing an aqueous extract from the material under conditions wherein 2018 component generation is controlled.

Suitably, the *Quillaja saponaria* Molina material is *Quillaja saponaria* Molina bark.

Typically, prior to the extraction, the *Quillaja saponaria* Molina plant materials are dried and milled. The harvested plant materials may be left to dry naturally and/or are dried partially or fully by being subject to heat. Suitably, when subjected to heating the drying temperature is in the range of 30-100° C., such as around 80° C., and may last for a few hours to 8 hours. Once dry, said plant materials are milled.

Any aqueous extraction process can be applied to obtain a crude aqueous saponin extract of *Quillaja saponaria* Molina in accordance with the invention. Solvent used for extraction will be substantially water but may include small amounts of other materials. The solvent will typically consist essentially of water, desirably the solvent is water. Extraction may take place in successive steps and be performed in a temperature ranging from 50° C. to 80° C. and may last from a couple of hours to 20 hours, such as 2 to 20 hours. Saponin crude extracts typically comprise a mixture of saponin species and non-saponin compounds, such as sugars, salts, polyphenols (tanins), solids in suspension and other lower molecular weight compounds. Prior to separating the different components in order to reach a purified saponin extract having a desired saponin profile, typically by a series of different chromatographic purification steps, the saponin crude extracts may be subject to clarification in order to remove impurities made of non-saponin compounds. Suitably, polymeric adsorbents, such as polyvinylpolypyrrolidone (PVPP), known to complex polyphenols, and/or clay-derived materials, such as bentonite, may be added to saponin crude extracts. Saponin crude extracts may additionally be concentrated, for example by nanofiltration or ultrafiltration. In order to obtain saponin crude extracts having a longer shelf life, said extracts may also be pasteurized, using high temperature, such as ranging from 40° to 95° C., suitably 60 to 90° C., especially about 86° C. Suitably pasteurization is performed for 10 minutes to 1 hour, more suitably 40 to 50 minutes. Antimicrobial agents may be used. An example of an antimicrobial agent is an antibacterial agent, such as sodium benzoate. A preservative may also be used. Suitably the crude aqueous extract is substantially sterile, and more suitably, sterile.

Suitably the step a) of selecting *Quillaja saponaria* Molina material having an appropriate 2018 component content comprises testing the 2018 component content of the *Quillaja saponaria* Molina material and/or determining the 2018 component content which would be obtained during aqueous extraction from the *Quillaja saponaria* Molina. Typically, the step of determining the 2018 component content which would be obtained during aqueous extraction from the *Quillaja saponaria* Molina comprises performing a small-scale extraction and determining the 2018 component content in the resulting extract. Suitably the small-scale extraction is performed on less than 500 g, such as less than 50 g, of *Quillaja saponaria* Molina material.

Suitably step b) is performed on at least 25 kg, such as 50 to 500 kg, such as 100 to 400 kg and in particular 200 to 300 kg of *Quillaja saponaria* Molina material.

While developing a process suitable for preparing a crude aqueous extract of *Quillaja saponaria* Molina in accordance with the invention, the present inventors observed that the pH along the process, in combination with high temperature, such as when pasteurizing, should be closely monitored and controlled. In particular, the inventors observed that combining low pH with high temperature may influence the stability of saponins and thus impact the saponin profile of an extract being processed, while high temperature on its own only triggered limited impact. Therefore, a balance between pH and temperature needs to be reached when preparing a saponin crude extract, depending on the saponin profile desired. In particular, the present inventors observed that the ratio of 2018 component/QS-21 main peak increases when a high temperature is combined with a low pH. Therefore, when using high temperature, such as during pasteurization, in combination with a low pH, such as when using a preservative like sodium benzoate, the time spent at high temperature should be limited to the maximum extent possible. For example, in order to quickly reach the pasteurization temperature, a heat exchanger may be used and/or the pasteurized crude aqueous extract of *Quillaja saponaria* Molina be cooled down rapidly, for example by immersion in cold water. Suitably the crude aqueous extract has a pH of 3 to 4.5, more suitably 3.6 to 4.0.

Crude Aqueous Extract Testing

In a fourth aspect of the invention, there is provided a method for determining the ratio of 2018 component/QS-21 main peak in a crude aqueous extract of *Quillaja saponaria* Molina, said method comprising the steps of:
(i) determining the 2018 component content in the crude aqueous extract of *Quillaja saponaria* Molina by UPLC-UV absorbance at 214 nm;
(ii) determining the QS-21 main peak content in the crude aqueous extract of *Quillaja saponaria* Molina by UPLC-UV absorbance at 214 nm; and
(iii) comparing the 2018 component content to the QS-21 main peak content to determine the ratio of 2018 component/QS-21 main peak.

In a fifth aspect of the invention, there is provided a method for identifying a crude aqueous extract of *Quillaja saponaria* Molina for use in the manufacture of a purified saponin extract, said method comprising the steps of:
(i) determining the ratio of 2018/QS-21 main peak by UPLC-UV absorbance at 214 nm; and
(ii) selecting a crude aqueous extract having a ratio of 2018 component/QS-21 main peak which is ≤0.075.

In one embodiment, the crude aqueous extract selected in step (ii) has a ratio of 2018 component/QS-21 main peak which is ≤0.064.

The invention will be further described by reference to the following, non-limiting, examples:

Example 1: Analytical Methods

HPLC-UV
Equipment
    Waters Alliance 2690/2695 separations module
    Waters 2487 UV Detector or 2996 PDA Detector
    Vydac Protein C4 4.6×250 mm 5 um column
    Mobile Phase A (MPA)—0.15% trifluoroacetic acid in water/acetonitrile (70:30 v/v)
    Mobile Phase B (MPB)—0.15% trifluoroacetic acid in acetonitrile
Linear Gradient Conditions:

| Time | Flow rate (ml/min) | % MPA | % MPB |
| --- | --- | --- | --- |
| 0 | 1 | 100 | 0 |
| 30 | 1 | 78.6 | 21.4 |
| 33 | 1 | 14.3 | 85.7 |

10 ul of sample is injected. UV detection is set at 214 nM.

Using a blank injection for reference, integration of peaks in the chromatogram provides a total absorbance. Peak of interest (e.g. QS-21 main peak) is compared to total absorbance to determine peak content as a percentage.

UPLC-UV
Equipment
    Waters Acquity UPLC
    Waters Acquity Tunable UV Detector
    Waters Acquity BEH C18 2.1×100 mm 1.7 um column
    Mobile Phase A (MPA)—0.025% acetic acid in water/acetonitrile (70:30 v/v)
    Mobile Phase B (MPB)—0.025% trifluoroacetic acid in water/acetonitrile (30:70 v/v)
Linear Gradient Conditions:

| Time | Flow rate (ml/min) | % MPA | % MPB |
| --- | --- | --- | --- |
| 0 | 0.5 | 88 | 12 |
| 10.2 | 0.5 | 65.7 | 34.3 |
| 11.2 | 0.5 | 10 | 90 |
| 13.2 | 0.5 | 10 | 90 |

Column temperature 28 degrees C. 10 ul of sample is injected. UV detection is set at 214 nM.

Using a blank injection for reference, integration of peaks in the chromatogram provides a total absorbance. Peak of interest (e.g. QS-21 main peak) is compared to total absorbance to determine peak content as a percentage.

Example 2: Crude Aqueous Extract of *Quillaja saponaria* Molina

A crude aqueous bark extract was separated by reverse phase HPLC using a C4 column and gradient elution: mobile phase A—water/acetonitrile, 7/3 v/v with 0.15% trifluoroacetic acid; mobile phase B—acetonitrile with 0.15% trifluoroacetic acid. UV detection was at 214 nm.

Crude aqueous bark extract samples are diluted as necessary with purified water. PVPP (60 mg/mL) was added, the mixture stirred for approximately 30 minutes, and then centrifuged to separate the PVPP resin from the supernatant.

The supernatant was then analysed to provide an HPLC-UV chromatogram.

Figure 1:
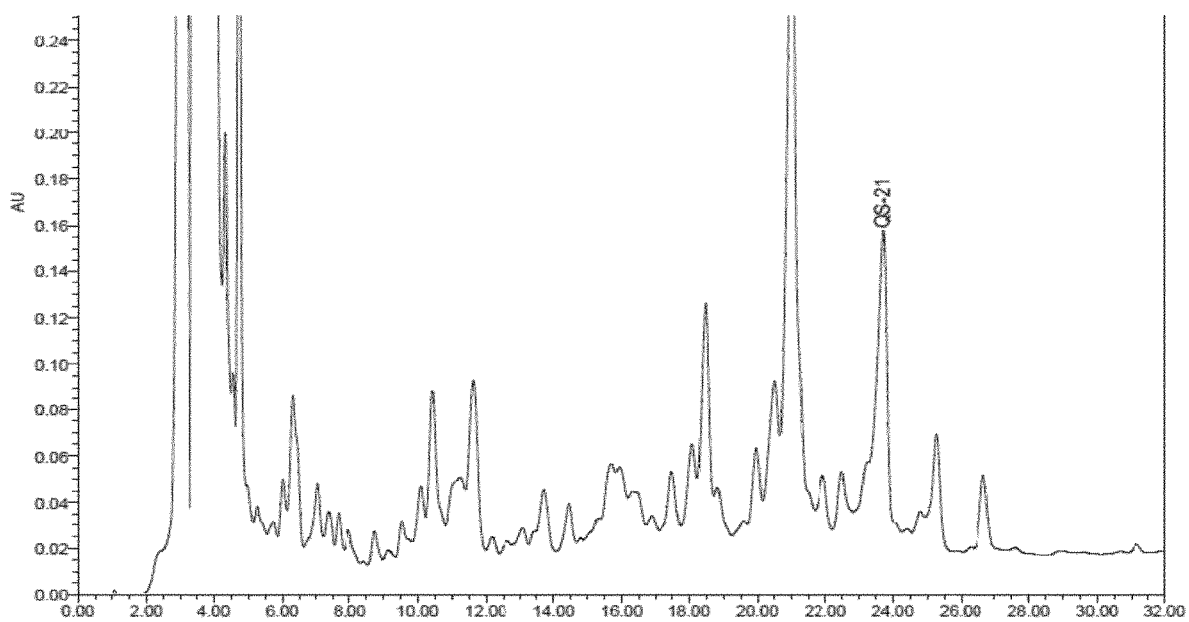
FIG. 1: HPLC chromatogram of a crude aqueous *Quillaja saponaria* Molina bark extract

FIG. 1 provides a representative example of an HPLC-UV chromatogram. The peak corresponding to the QS-21 fraction is indicated.

Example 3: UPLC-UV of an Aqueous Saponin Crude Bark Extract of *Quillaja saponaria* Molina Tree A sample of crude aqueous bark extract of *Quillaja saponaria* Molina was analysed by the HPLC-UV and UPLC-UV methods described in Example 1.

FIG. 2 provides the results of the HPLC-UV and FIG. 3 provides the results of the UPLC-UV.

By determining the peak area for the particular components (QS-21 main peak, 2018 component or Preceding peak) it is possible to calculate the ratios of the components in the crude extract.

Example 4: Effect of pH and Temperature on the 2018 Component/QS-21 Ratio

Figure 5:
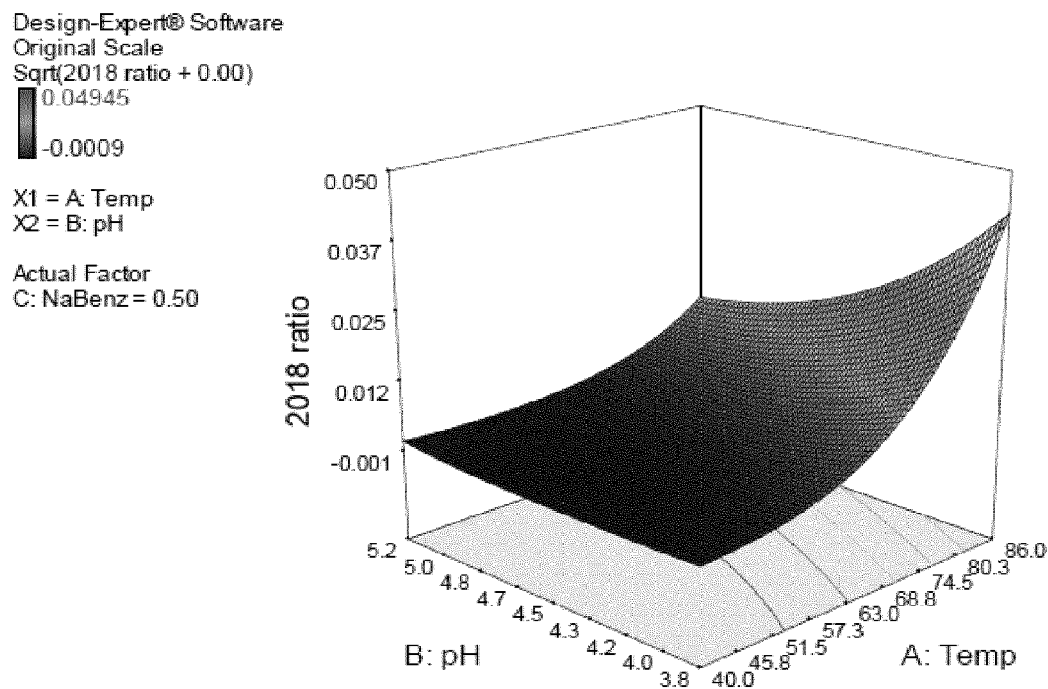
Figure 6:
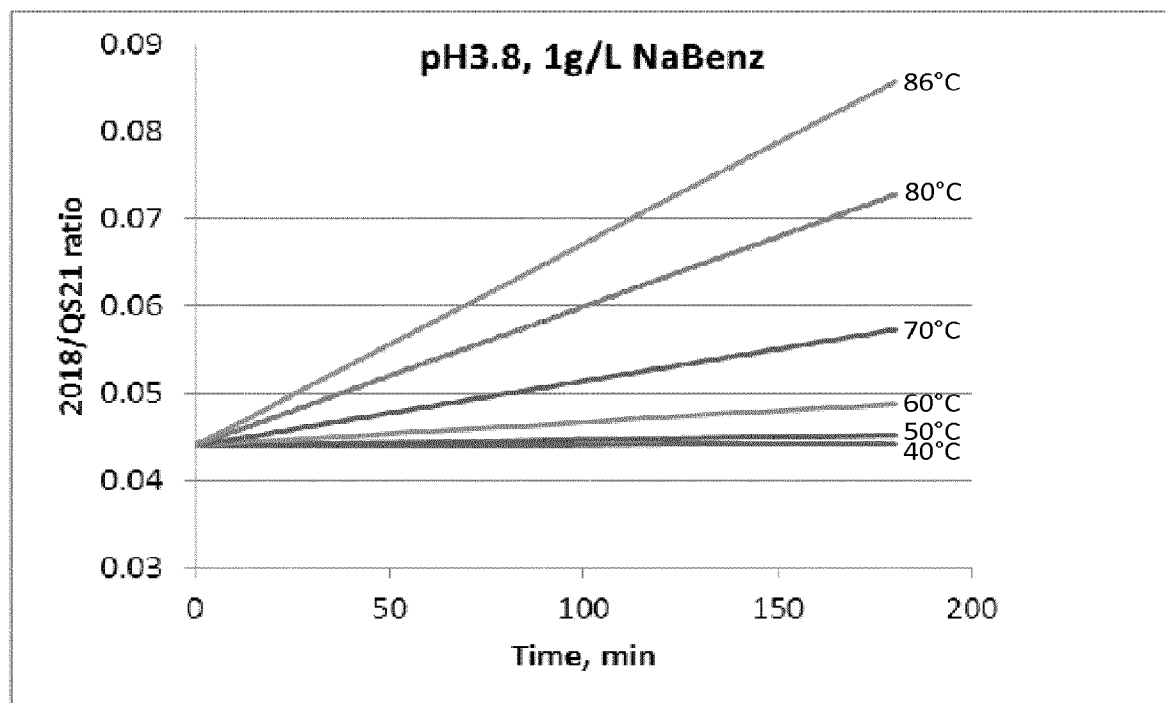

Multiple samples of crude aqueous extract of *Quillaja saponaria* Molina were prepared according to the methods described herein. On each occasion, the temperature, pH or quantity of sodium benzoate was varied during the pasteurisation phase and the change in 2018 component/QS-21 main peak ratio was measured after 3 hours. The results are provided in FIG. 4. The impact of pH and temperature variation is represented graphically in FIG. 5. The impact of different temperatures over time at constant pH 3.8 is illustrated in FIG. 6.

Temperature was found to be directly proportional to the 2018 component/QS-21 main peak ratio, except at or below 40° C. during this 3 hour range tested, where the ratio does not seem to change regardless of the pH or sodium benzoate conditions. pH was found to be inversely proportional to the 2018 component/QS-21 main peak ratio, especially at lower pHs.

Sodium benzoate only had a minor effect on the 2018 component/QS-21 main peak ratio at elevated temperatures.

In summary, it was found that varying pH and temperature had a substantial impact on the 2018 component/QS-21 main peak ratio, with higher temperatures and lower pH increasing the ratio.

Consequently, in order to obtain a crude aqueous extract of *Quillaja saponaria* Molina with appropriate levels of 2018 component, careful selection of *Quillaja saponaria* Molina raw material and processing in a manner which limits excessive 2018 component generation is necessary.

Example 5: Large Scale Production of Crude Aqueous Extract of *Quillaja saponaria* Molina Having Defined 2018 Component Composition Bark Selection Sample lots of approximately 37 g were taken from a range of batches of *Quillaja saponaria* Molina bark material. The samples were separately subjected to aqueous extraction at around 65° C. for approximately 5 hours. The extract was treated with PVPP, filtered and concentrated. pH was adjusted to 3.9 before the addition of sodium benzoate (0.1%) and pasteurisation performed at 86° C. for 45 minutes.

2018 component (using UPLC-UV) and Preceding peak content (using HPLC-UV) was then determined. Based on the results, batches of *Quillaja saponaria* Molina bark material were selected for use in full scale extraction.

Although individual batches may not meet target specification, to maximise yield it is possible to combine individual batches which are outside target specification with other batches (e.g. high content with low content) such that an overall average within target specification is achieved.

Main Extraction

Approximately 280 kg of *Quillaja saponaria* Molina bark material selected for 2018 component content was subjected to aqueous extraction at around 70° C. for at least 2 hours. Following extraction, the pH was adjusted to 3.8. The extract was treated with PVPP, filtered and concentrated. pH was verified and adjusted again if necessary before the addition of sodium benzoate (0.1%) and pasteurisation performed at 86° C. for 45 minutes. Pasteurised material was quickly cooled to minimise the time at elevated temperature, thereby providing a solution of crude aqueous extract of *Quillaja saponaria* Molina.

Crude aqueous extract was analysed by HPLC-UV (Preceding peak/QS21 main peak ratio) and UPLC-UV (2018 component/QS21 main peak ratio).

Bark selection and control of pH and temperature exposure ensured that crude bark extract consistently met the desired specification. In the absence of bark selection and control of pH and temperature exposure, crude aqueous extract frequently failed to meet specification.

The use of the process as described in Example 5 can consistently provide a crude aqueous bark extract of *Quillaja Saponaria* Molina having a defined ratio of 2018 component/QS-21 main peak, such as consistently ≤0.075, and presenting a chromatographic profile comparable to the chromatogram shown in FIG. 3.

BIBLIOGRAPHY

Dalsgaard et al. 1974 "Saponin adjuvants", Archiv. für die gesamte Virusforschung, Vol. 44, Springer Verlag, Berlin, p 243-254

De Becker, G., V. Moulin, B. Pajak, C. Bruck, M. Francotte, C. Thiriart, J. Urbain, and M. Moser. 2000. The adjuvant monophosphoryl lipid A increases the function of antigen-presenting cells. *International immunology.* 12:807-815.

Didierlaurent A. M., Collignon C., Bourguignon P., Wouters S., Fierens K., Fochesato M., Dendouga N., Langlet C., Malissen B., Lambrecht B. N., Garcon N., Van Mechelen M., and S. Morel. 2014 Enhancement of Adaptive Immunity by the Human Vaccine Adjuvant AS01 Depends on Activated Dendritic Cells *Journal of Immunology* 193 (4):1920-1930.

Didierlaurent et al, 2017 Adjuvant system AS01: helping to overcome the challenges of modern vaccines *Expert Reiews of Vaccines* 16 (1): 55-63

Garcon, N., and M. Van Mechelen. 2011. Recent clinical experience with vaccines using MPL- and QS-21-containing adjuvant systems. *Expert review of vaccines.* 10:471-486

Ismaili, J., J. Rennesson, E. Aksoy, J. Vekemans, B. Vincart, Z. Amraoui, F. Van Laethem, M. Goldman, and P. M. Dubois. 2002. Monophosphoryl lipid A activates both human dendritic cells and T cells. *Journal of immunology.* 168:926-932.

Kensil, C. R., U. Patel, M. Lennick, and D. Marciani. 1991. Separation and characterization of saponins with adjuvant activity from *Quillaja saponaria* Molina cortex. *Journal of immunology.* 146:431-437.

Kensil, C. R., and R. Kammer. 1998. QS-21: a water-soluble triterpene glycoside adjuvant. *Expert opinion on investigational drugs.* 7:1475-1482.

Lambrecht, B. N., M. Kool, M. A. Willart, and H. Hammad. 2009. Mechanism of action of clinically approved adjuvants. *Current opinion in immunology.* 21:23-29.

Leroux-Roels I. et al. J. Infect. Dis. 2012, 206: 1280-1290

Li, H., S. B. Willingham, J. P. Ting, and F. Re. 2008. Cutting edge: inflammasome activation by alum and alum's adjuvant effect are mediated by NLRP3. *Journal of immunology.* 181:17-21.

Livingston, P. O., S. Adluri, F. Helling, T. J. Yao, C. R. Kensil, M. J. Newman, and D. Marciani. 1994. Phase 1 trial of immunological adjuvant QS-21 with a GM2 ganglioside-keyhole limpet haemocyanin conjugate vaccine in patients with malignant melanoma. *Vaccine.* 12:1275-1280.

Ragupathi, G., J. R. Gardner, P. O. Livingston, and D. Y. Gin. 2011. Natural and synthetic saponin adjuvant QS-21 for vaccines against cancer. *Expert review of vaccines.* 10:463-470

Martin, M., S. M. Michalek, and J. Katz. 2003. Role of innate immune factors in the adjuvant activity of monophosphoryl lipid A. *Infection and immunity.* 71:2498-2507.

Marty-Roix, R. et al. Identification of QS-21 as an Inflammasome-activating Molecular Component of Saponin Adjuvants. *J. Biol. Chem.* 291, 1123-36 (2016)

Mata-Haro, V., C. Cekic, M. Martin, P. M. Chilton, C. R. Casella, and T. C. Mitchell. 2007. The vaccine adjuvant monophosphoryl lipid A as a TRIF-biased agonist of TLR4. *Science.* 316:1628-1632.

Newman, M. J., J. Y. Wu, B. H. Gardner, K. J. Munroe, D. Leombruno, J. Recchia, C. R. Kensil, and R. T. Coughlin. 1992. Saponin adjuvant induction of ovalbumin-specific CD8+ cytotoxic T lymphocyte responses. *Journal of immunology.* 148:2357-2362.

Soltysik, S., J. Y. Wu, J. Recchia, D. A. Wheeler, M. J. Newman, R. T. Coughlin, and C. R. Kensil. 1995. Structure/function studies of QS-21 adjuvant: assessment of triterpene aldehyde and glucuronic acid roles in adjuvant function. *Vaccine.* 13:1403-1410.

We claim:

1. A composition comprising a crude aqueous extract of *Quillaja saponaria* Molina and an exogenous antimicrobial agent; the crude aqueous extract of *Quillaja saponaria* Molina comprising a QS-21 main peak and a 2018 component; the composition having a 2018 component: QS-21 main peak ratio of less than or equal to 0.075:1; and the 2018 component: QS-21 main peak ratio being a peak area of the 2018 component, as measured by absorbance of ultraviolet (UV) light at a wavelength of 214 nm, to the peak area of the QS-21 main peak, as measured by absorbance of UV light at the wavelength of 214 nm.

2. The composition of claim 1, wherein the 2018: component: QS-21 main peak ratio is less than or equal to 0.064:1.

3. The composition of claim 1, wherein the QS-21 main peak is at least 1 g per L of the composition.

4. The composition of claim 1, wherein the QS-21 main peak is at least 2 g per L of the composition.

5. The composition of claim 1, wherein the crude aqueous extract of *Quillaja saponaria* Molina is extracted from *Quillaja saponaria* Molina bark.

6. The composition of claim 1 being pasteurized.

7. The composition of claim 1, wherein the exogenous antimicrobial agent is sodium benzoate.

8. The composition of claim 1 having a pH from 3.0 to 4.5.

9. A method for preparing the composition of claim 1, the method comprising the following steps:
(a) providing a candidate *Quillaja saponaria* Molina material, the candidate *Quillaja saponaria* Molina material being at least 25 kg;
(b) obtaining a sample from the candidate *Quillaja saponaria* Molina material, the sample being less than 500 g;
(c) performing an aqueous extraction on the sample, thereby obtaining a small-scale extract;
(d) determining the 2018 component: QS-21 main peak ratio of the small-scale extract;
(e) selecting the candidate *Quillaja saponaria* Molina material, which has the 2018 component: QS-21 main peak ratio of less than or equal to 0.075:1, thereby obtaining a selected *Quillaja saponaria* Molina material;
(f) preparing the crude aqueous extract of *Quillaja saponaria* Molina from the selected *Quillaja saponaria* Molina material; and
(g) adding the exogenous antimicrobial agent to the crude aqueous extract of *Quillaja saponaria* Molina.

10. The method of claim 9, wherein the sample is less than 50 g.

11. The method of claim 9, wherein in step (a), the candidate *Quillaja saponaria* Molina material is at least 500 kg.

12. The method of claim 9, wherein step (f) comprises treating the crude aqueous extract of *Quillaja saponaria* Molina with polyvinylpolypyrrolidone (PVPP).

13. The method of claim 12, wherein the pH is maintained from 3.0 to 4.5 before the treating with the PVPP.

14. The method of claim 9 further comprising step (h) pasteurizing, thereby obtaining a pasteurized composition.

15. The method of claim 14, wherein the pasteurizing is performed at 60° C. to 90° C.

16. The method of claim 14, wherein between steps (f) and (g), the crude aqueous extract of *Quillaja saponaria* Molina is maintained at a pH from 3.0 to 4.5.

17. The method of claim 9, wherein the antimicrobial agent is an antibacterial agent.

18. The method of claim 14, wherein the pasteurizing is performed for 10 minutes to 1 hour.

19. The method of claim 14 further comprising actively cooling the pasteurized composition.

20. The method of claim 9, wherein the candidate *Quillaja saponaria* Molina material is *Quillaja saponaria* Molina bark.

21. The method of claim 9, wherein the 2018 component: QS-21 main peak ratio is less than or equal to 0.064:1.

22. A composition comprising a crude aqueous extract of *Quillaja saponaria* Molina and an exogenous antimicrobial agent; the crude aqueous extract of *Quillaja saponaria* Molina comprising a 2018 component and a QS-21 main peak; the QS-21 main peak comprising a 1856 component, a 1988 component, and a 2002 component; the 2018 component having a monoisotopic molecular weight of 2017.9 g per mole; the 1856 component having a monoisotopic molecular weight of 1855.9 g per mole; the 1988 component having a monoisotopic molecular weight of 1987.9 g per mole; the 2002 component having a monoisotopic molecular weight of 2001.9 g per mole; the composition having a 2018 component: QS-21 main peak ratio of less than or equal to 0.075:1; and the 2018 component: QS-21 main peak ratio being a peak area of the 2018 component, as measured by absorbance of UV light at a wavelength of 214 nm, to the peak area of the QS-21 main peak, as measured by absorbance of UV light at the wavelength of 214 nm.

23. The composition of claim 22, wherein the 2018:component: QS-21 main peak ratio is less than or equal to 0.064:1.

24. The composition of claim 22, wherein the QS-21 main peak is at least 1 g per L of the composition.

25. The composition of claim 22, wherein the QS-21 main peak is at least 2 g per L of the composition.

26. The composition of claim 22, wherein the crude aqueous extract of *Quillaja saponaria* Molina is extracted from *Quillaja saponaria* Molina bark.

27. The composition of claim 22 being pasteurized.

28. The composition of claim 22, wherein the exogenous antimicrobial agent is sodium benzoate.

29. The composition of claim 22 having a pH from 3.0 to 4.5.

30. A method for preparing the composition of claim 22, the method comprising the following steps:
(a) providing a candidate *Quillaja saponaria* Molina material, the candidate *Quillaja saponaria* Molina material being at least 25 kg;
(b) obtaining a sample from the candidate *Quillaja saponaria* Molina material, the sample being less than 500 g;
(c) performing an aqueous extraction on the sample, thereby obtaining a small-scale extract;
(d) determining the 2018 component: QS-21 main peak ratio of the small-scale extract;
(e) selecting the candidate *Quillaja saponaria* Molina material, which has the 2018 component: QS-21 main peak ratio of less than or equal to 0.075:1, thereby obtaining a selected *Quillaja saponaria* Molina material;
(f) preparing the crude aqueous extract of *Quillaja saponaria* Molina from the selected *Quillaja saponaria* Molina material; and
(g) adding the exogenous antimicrobial agent to the crude aqueous extract of *Quillaja saponaria* Molina.

31. The method of claim 30, wherein the sample is less than 50 g.

32. The method of claim 30, wherein in step (a), the candidate *Quillaja saponaria* Molina material is at least 500 kg.

33. The method of claim 30, wherein step (f) comprises treating the crude aqueous extract of *Quillaja saponaria* Molina with PVPP.

34. The method of claim 33, wherein the pH is maintained from 3.0 to 4.5 before the treating with the PVPP.

35. The method of claim 30 further comprising step (h) pasteurizing, thereby obtaining a pasteurized composition.

36. The method of claim 35, wherein the pasteurizing is performed at 60° C. to 90° C.

37. The method of claim 35, wherein between steps (f) and (g), the crude aqueous extract of *Quillaja saponaria* Molina is maintained at a pH from 3.0 to 4.5.

38. The method of claim 30, wherein the antimicrobial agent is an antibacterial agent.

39. The method of claim 35, wherein the pasteurizing is performed for 10 minutes to 1 hour.

40. The method of claim 35 further comprising actively cooling the pasteurized composition.

41. The method of claim 30, wherein the candidate *Quillaja saponaria* Molina material is *Quillaja saponaria* Molina bark.

42. The method of claim 30, wherein the 2018 component: QS-21 main peak ratio is less than or equal to 0.064:1.

* * * * *